United States Patent [19]

Dubé

[11] Patent Number: 4,992,324
[45] Date of Patent: Feb. 12, 1991

[54] ABSORBENT FLEXIBLE BOARD

[75] Inventor: Emile C. Dubé, Montreal East, Canada

[73] Assignee: Johnson & Johnson, Inc., Montreal, Canada

[21] Appl. No.: 242,271

[22] Filed: Sep. 12, 1988

[51] Int. Cl.$^5$ ............................................. D03D 3/00
[52] U.S. Cl. .................................... 428/226; 428/105; 428/225; 428/229; 428/913; 428/284
[58] Field of Search ............... 428/105, 109, 257, 258, 428/259, 913, 232, 294, 225, 226, 227, 229, 284

[56] References Cited

U.S. PATENT DOCUMENTS 3,903,879  9/1975  Riley et al. ..................... 428/259
4,670,326  6/1987  Heiman .......................... 428/259

Primary Examiner—James J. Bell
Attorney, Agent, or Firm—Joseph F. Shirtz

[57] ABSTRACT

A highly flexible absorbent material useful in sanitary napkins, diapers and the like is obtained by preparing an absorbent board which includes integral reinforcing fibers, and partially shearing the board into a plurality of narrow strips without substantially cutting or breaking the reinforcing fibers. The resulting material is extremely flexible in the transverse direction and maintains its integrity due to the presence of the reinforcing fibers which interconnect adjacent strips. The absorbent material is preferably composed of a mixture of peat moss and synthetic reinforcing fibers.

19 Claims, 3 Drawing Sheets

ABSORBENT FLEXIBLE BOARD

This application is related to commonly assigned, co-pending patent application Ser. No. 242,274 filed Sept. 12, 1988, entitled "Apparatus for Partially Slitting Absorbent Boards".

FIELD OF INVENTION

This invention relates to an absorbent material useful in products such as sanitary napkins, diapers, tampons and the like, and more particularly, to a highly flexible absorbent board comprising a partially sheared, fiber reinforced peat moss or similar absorbent material. This invention also relates to a method for the manufacture of such flexible absorbent boards.

BACKGROUND OF THE INVENTION

Absorbent materials in the form of relatively thin, dense, sheet-like structures resembling heavy weight paper or paperboard are referred to as absorbent boards to distinguish such materials from loose, bulky absorbents such as wood pulp, fluff, and the like. Absorbent boards may be formed of a variety of materials of natural and/or synthetic origin. For example, absorbent boards may be prepared from wood pulp, peat moss, and mixtures thereof, optionally including other components such as reinforcing synthetic textile fibers, binders, surfactants and the like. Such boards are commonly prepared by wet laying a slurry of the solid components of the board on conventional papermaking equipment as described, for example, in U.S. Pat. No. 4,507,122, incorporated herein by reference. Absorbent boards comprising a hydrophilic fibrous material such as rayon or wood pulp and superabsorbent hydrogel polymers may be prepared by a dry process in which the fibrous mixture is mechanically compressed to a high density as described, for example, in U.S. Pat. Nos. 4,340,556 and 4,610,678.

In accordance with the teachings of U.S. Pat. No. 4,507,122, a laminate structure comprising a thin layer of Kraft paper and a heavier layer of a mixture of peat moss and wood pulp is prepared by sequentially depositing the materials from aqueous slurry in a wet process on conventional papermaking equipment. The deposited solids are dewatered, partially dried and compressed to a density of from about 0.2 to 1.0 g/cm³. The resulting absorbent board is relatively stiff, and flexibility may be increased by mechanical working such as embossing or micro corrugating. The reference further suggests that the flexibility of the board may be increased by slitting.

Mechanical working of stiff absorbent boards to increase the flexibility thereof is also disclosed for example, in U.S. Pat. No. 4,605,402. In accordance with this reference an absorbent board composed of a web of synthetic fibers impregnated with polymeric superabsorbent is compressed and bonded to form a composite structure. As prepared, the structure is relatively stiff and is processed to increase softness and flexibility by micro corrugation and perfembossing.

The use of peat moss in absorbent structures, usually in combination with other absorbent materials such as wood pulp, has been the subject of many recent patents. U.S. Pat. No. 4,473,440 discloses the preparation of a peat moss board by wet laying a slurry of peat moss onto a predeposited layer of Kraft paper, dewatering and conditioning the board to a specific water content, and then densifying the board by calendering to obtain a highly absorbent material. Wetting agents, coloring agents, adhesives and the like, may be incorporated into the system as desired.

U.S. Pat. No. 4,676,871 discloses an absorbent board comprising a mixture of peat moss with from about 1 to 15% by weight polyester staple fibers as a reinforcing material, and treated with a surfactant to enhance wetability. The board is prepared by air laying to form a low density product followed by calendering to a final density of about 0.7 g/cc.

U.S. Pat. No. 4,226,237 discloses a composite absorbent structure for use in sanitary napkins, diapers and the like, comprising a first layer of cellulose fibers, a second layer of a mixture of peat moss and wood pulp, and an optional third layer of additional cellulose fibers. The peat moss layer may be loosely associated or stabilized with adhesives.

U.S. Pat. No. 4,215,692 discloses an absorbent structure comprising a mixture of peat moss with mechanical wood pulp and optionally with other absorbent materials such as long fibered chemical wood pulp, rayon or the like. Although the absorbent structure is first produced in the form of a board by wet laying, the board is subsequently ground to provide a fluffed material for use in the absorbent products.

Other patent references deal with the treatment of peat moss to enhance its properties for use in absorbent products such as bleaching (U.S. Pat. No. 4,170,515), treating with anti-microbials (U.S. Pat. No. 4,618,496), and grafting with polymeric compositions (U.S. Pat. No. 4,305,393).

The present invention is concerned with a novel absorbent structure composed of peat moss, wood pulp, mixtures thereof or other compacted friable absorbent material. It is an object of the present invention to provide an absorbent board of such materials having improved flexibility in at least one direction, while retaining the overall structural integrity of the board. It is a further object of this invention to provide a longitudinal absorbent board comprising peat moss which is highly flexible in its transverse direction and moderately flexible in the longitudinal direction. It is a yet further object of this invention to provide a relatively thin, highly absorbent, highly flexible absorbent element suitable for use as the primary absorbent in sanitary napkins, diapers, and the like. These and other objects of the present invention will be more readily understood from the ensuing description of the invention.

SUMMARY

The absorbent structure of the present invention comprises a plurality of narrow, longitudinally extending strips disposed adjacent to one another and interconnected by an integral fibrous component extending between adjacent strips. The absorbent structure is preferably fabricated from a calendered peat moss board having a fibrous component admixed therewith. The fibrous component is suitably a natural or synthetic textile fiber such as rayon, polyester, nylon, acrylic or the like, having a length of from about 0.25 to 1.5 inches and a denier of from about 1.0 to 5. The fibrous component may be present in an amount from about 2 to 20% by weight, most preferably from 4 to 8%. The absorbent board may also comprise other components such as wood pulp, synthetic wood pulp, polymers, surfactants, superabsorbents and the like.

The absorbent structure comprising peat moss as the primary absorbent component is formed as a board by air or wet laying and calendering to obtain a relatively thin, i.e. from about 0.01 to 0.05 inch thick, relatively dense, i.e. from about 0.2 to 1.0 g/cm$^3$, sheet like structure. The structure may include a layer of Kraft tissue laminated on one or both surfaces of the peat moss layer. The absorbent board thus formed is a relatively thin but stiff structure similar to those described in the aforementioned U.S. patent references.

The absorbent peat moss board or other suitable compacted absorbent structure is processed in accordance with the present invention to increase the flexibility thereof by partially severing the structure into a plurality of narrow strips which remain interconnected by an integral fibrous component of the structure. The board may be suitably severed by passing between a pair of rolls having a plurality of parallel spaced apart ridges or teeth extending circumferentially around the outer surface of the rolls. The two rolls are adjusted so that the opposing teeth are offset from each other without contact so that when the absorbent board is passed between the rolls, alternate strips of the friable board material are displaced relative to one another in the plane of the board. The displacement is sufficient to disrupt the friable absorbent material of the board such as the peat moss or wood pulp and delineate the individual strips without cutting or otherwise substantially disrupting the fibrous component of the board.

The partially severed product consists of a plurality of individual strips of the absorbent board having a width corresponding to the spacing of the teeth on the shearing rolls, and interconnected by the fibrous component extending between adjacent strips. The fibrous component provides a hinge-like action, and the resulting product has extreme transverse flexibility while maintaining transverse structural integrity The partial shearing only marginally improves flexibility in the longitudinal direction of the strips however, and if greater flexibility is desired, the absorbent board may be embossed or micro corrugated in a generally transverse direction before or after the partial shearing operation.

In addition to increasing transverse flexibility, partial shearing of the absorbent board enhances the rate of liquid absorption by increasing the effective surface area of the board as a result of the edges of the sheared material being available to the fluid. The partial shearing also imparts directional absorbent capacity to the absorbent boards since fluid wicks preferentially along the slits in the longitudinal direction of the material. By orienting the slit material in the longitudinal direction of a sanitary napkin or diaper, the incidence of edge failure in such products is consequently reduced.

The fibrous component extending between and interconnecting adjacent strips of absorbent material permits the absorbent element to be transported, rolled and handled during processing and assembly of absorbent products. The enhanced rate of fluid absorption and the directional absorption characteristics of the absorbent element permit it to be used directly as the primary absorbent in absorbent products with the resulting products being exceptionally thin, flexible and effective.

DETAILED DESCRIPTION

Figure 1:
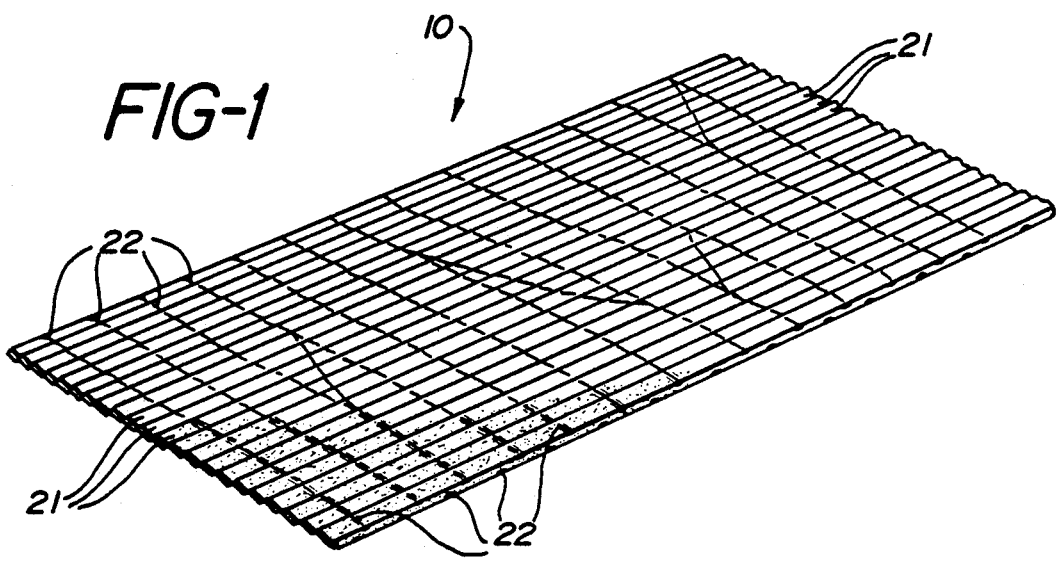
FIG. 1 is a perspective view of a partially sheared absorbent element in accordance with the present invention.
Figure 2:
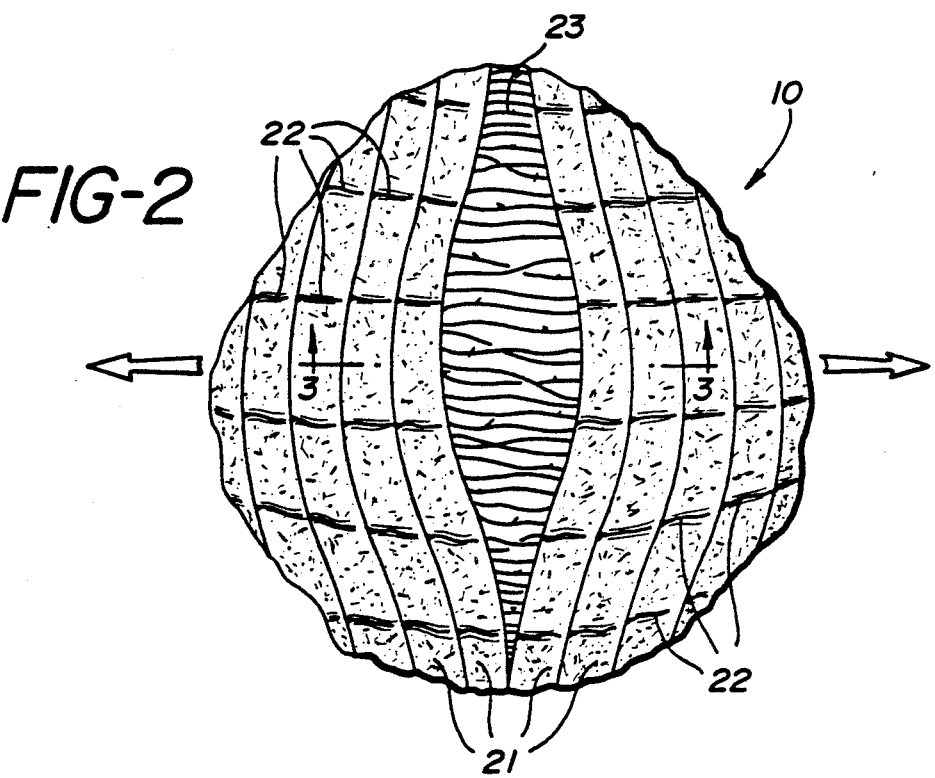
FIG. 2 is an enlarged top plane view of a portion of the absorbent element of FIG. 1 with the separation of two strips exaggerated to illustrate the interconnecting fibrous component.
Figure 3:
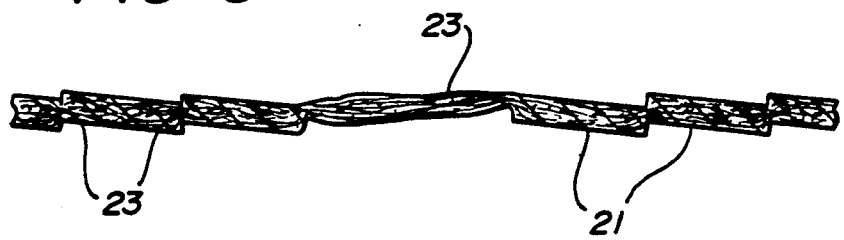
FIG. 3 is a cross sectional end view through line 3—3 of FIG. 2.

Referring now to FIG. 1-3, there is illustrated absorbent element 10 comprising a plurality of longitudinally extending strips 21 interconnected by fibrous means 23 extending between adjacent strips. In the illustrated preferred embodiments, absorbent element 10 also evidences a plurality of generally transverse extending surface ridges 22 resulting from embossing the absorbent board prior to forming strips 21, in order to improve the longitudinal flexibility of the final product.

The board is preferably composed of peat moss, wood pulp or a mixture thereof as the absorbent material. The absorbent board is formed by air laying or wet laying a mixture of the absorbent material and a reinforcing fibrous component followed by calendering in accordance with procedures generally known in the art as described, for example, in U.S. Pat. Nos. 4,676,871, 4,507,122 and 4,473,440 which are incorporated here by reference for their teaching of materials and processing conditions. The absorbent peat moss board, at the time of embossing or partial shearing, typically has a density of from about 0.2 to 1.5 g/cc, and most preferably from about 0.5 to 1.0 g/cc, with a thickness of from about 0.01 to 0.10 inches, most preferably from about 0.01 to 0.05 inches. The board may be partially sheared into strips having a width of from about 2.0 to 10 mm or wider. In a particularly preferred embodiment, the absorbent board is composed of a peat moss core laminated between layers of Kraft tissue which further stabilize the peat moss and reduces surface sloughing during processing and handling.

As described above, the peat moss may be used alone or in combination with wood pulp, or wood pulp may be used alone as a major absorbent component of the board. In all cases however, the board contains an additional fibrous reinforcing component which serves to reinforce the peat moss and/or wood pulp material. Whereas peat moss and wood pulp are fibrous materials, the fibrous length of these materials is generally less than about 6.5 millimeters. As used herein, the term "reinforcing component" refers to a natural or synthetic material having a fiber length of at least 0.25 inches and preferably from about 0.5 to 1.0 inches, although longer so that the fibers are not separated from adjacent strips during the partial shearing operation and are, in fact, retained in each adjacent strip with sufficient tenacity to resist pulling free during normal handling and processing of the partially sheared material. The minimum acceptable fiber length of the reinforcing component will accordingly depend to some extent on the composition of the absorbent material, including whether or not binders are present, and on the width of the strips formed during the partial shearing operation.

The reinforcing component is preferably a synthetic fiber such as polyester fiber of from 1 to 5 denier and having staple length of from 0.5 to 1 inches. The polyester fiber is blended with the peat moss and/or wood pulp to form a uniform mixture before forming the absorbent board. The polyester fiber is preferably added in an amount equal to from 2 to 20% by weight of the dry components of the absorbent board, and most preferably in an amount from about 4 to 8% by weight.

Figure 4:
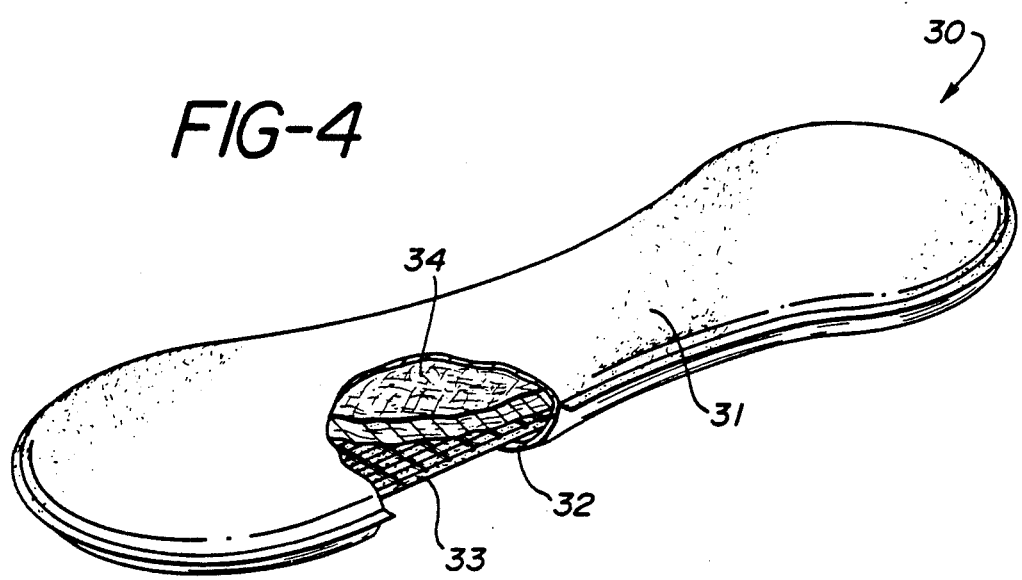
FIG. 4 is a perspective view of a sanitary napkin utilizing the absorbent element of FIG. 1.
Figure 5:
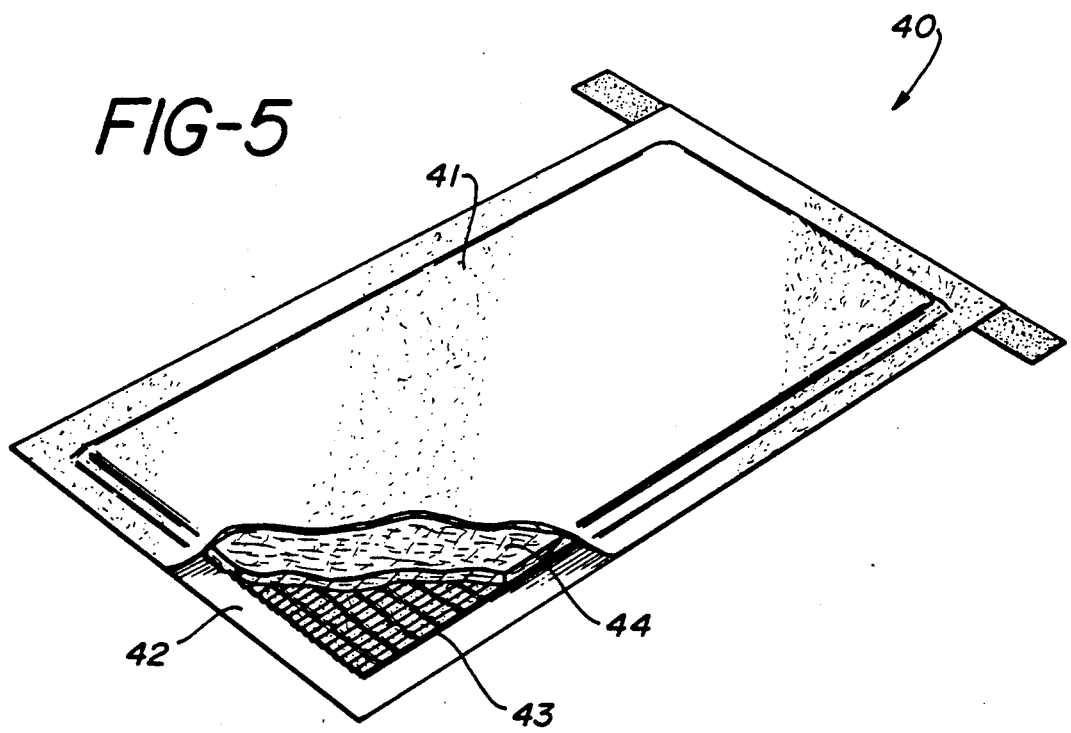
FIG. 5 is a perspective view of a disposable diaper utilizing the absorbent element of FIG. 1.

The partially severed absorbent element may be utilized as the primary absorbent in absorbent products such as sanitary napkins and diapers of generally conventional construction as illustrated in FIGS. 4 and 5 respectively. The flexible absorbent element of the present invention is readily utilized to produce thin, flexible absorbent products. As illustrated in FIG. 4, the absorbent element is preferably incorporated in a sanitary napkin with the strips of the element oriented in the longitudinal direction of the napkin. Thus oriented, the absorbent element provides good transverse flexibility and the partially severed strips promote the distribution of fluids in the longitudinal direction of the napkin to minimize edge failure.

With further reference to FIG. 4, there is illustrated sanitary napkin 30 comprising liquid permeable cover fabric 31, liquid impermeable backing film 32, the absorbent element of this invention 33, and an intermediate layer 34 of cellulosic fibers such as wood pulp fluff between the absorbent element and cover 31. The cover is sealed to the backing material around the perimeter of the napkin to enclose the absorbent components. The intermediate layer 34 is an optional component which is preferably included to aid in fluid distribution and to impart softness to the body facing side of the napkin. The napkin of FIG. 4 is of a very simple construction incorporating only the most basic components and is presented simply for purposes of illustration, it being understood that the absorbent element of the present invention may be utilized in any desired napkin construction.

FIG. 5 illustrates a baby diaper having a construction similar to that of the sanitary napkin of FIG. 4. In FIG. 5, diaper 40 consists of liquid permeable cover 41, liquid impermeable backing film 42, the absorbent element of the present invention 43, and cellulosic fluff 44. Cover 41 is sealed to backing 42 around the perimeter of the diaper to enclose the absorbent components 43 and 44.

Absorbent products including the flexible absorbent element of the present invention may also include other components such as one or more layers of wood pulp fluff for softness and bulk, superabsorbents to increase fluid retention properties, embossed channels to aid in fluid distribution, and the like, all of which are well known in the art pertaining to such absorbent products. Yet other absorbent products and variations in the construction thereof utilizing the absorbent element of the present invention will be immediately apparent to those skilled in the art, as illustrated for example in U.S. Pat. No. 4,226,237, incorporated herein by reference for its disclosure of absorbent structures, products and materials of construction.

Figure 6:
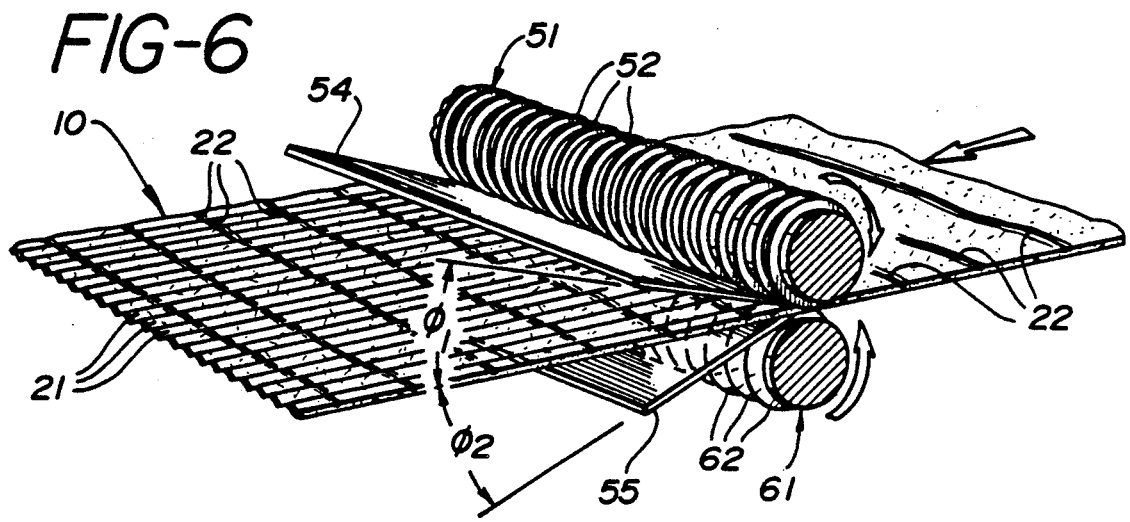
FIG. 6 is an illustration of one device suitable for partially shearing an absorbent board to produce the absorbent element of FIG. 1.
Figure 7:
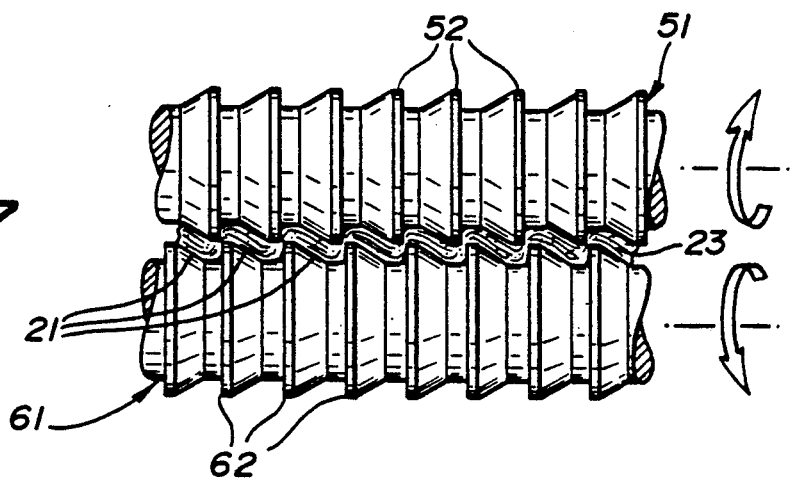
FIG. 7 is an illustration of a preferred arrangement for the cutting teeth in the device of FIG. 6.
Figure 8:
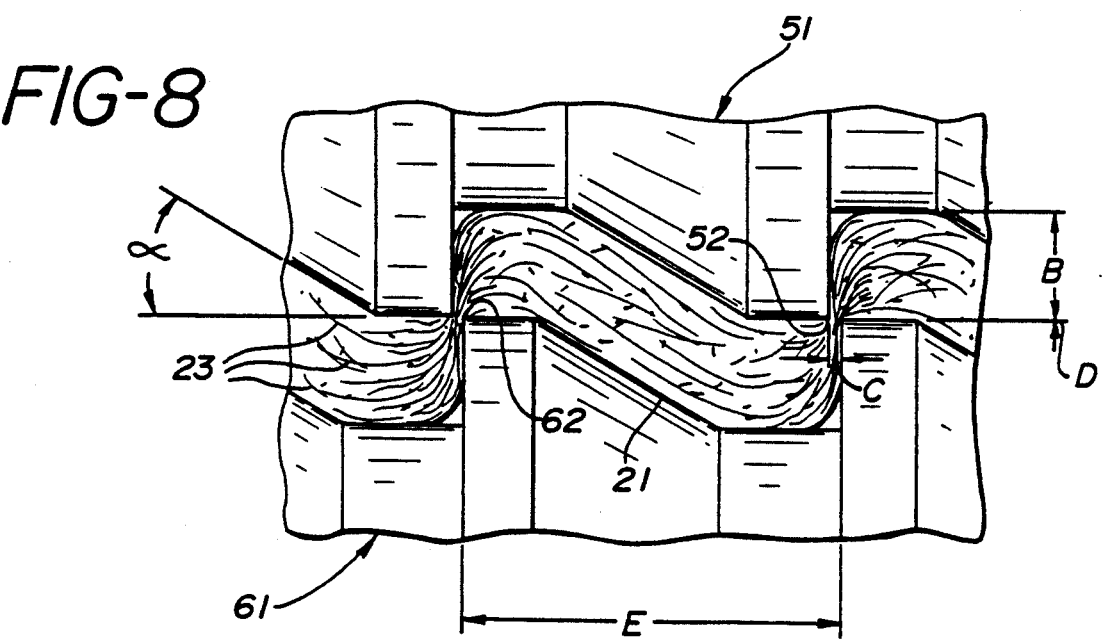
FIG. 8 is an enlarged view of a portion of the cutting teeth of FIG. 7 illustrating the teeth in greater detail and indicating important dimensions.

Referring now to FIGS. 6–8 of the present application, there is illustrated one device which may be used with good results to produce the partially severed absorbent elements of the present invention. The illustrated device consists of a pair of opposing rolls 51 and 61, each having a plurality of cutting teeth 52 and 62 disposed on the surface of the rolls in parallel, circumferentially extending bands. The cutting teeth are most preferably disposed in a sawtooth array as illustrated in FIG. 7. Doctor blades 54 and 55 include projections (not shown) which extend into the spaces between the cutting teeth on rolls 51 and 61, respectively to assure clean separation between the partially severed strips 21 and the cutting rolls. Angles $\phi_1$ and $\phi_2$ are adjusted to obtain optimum performance and are usually within the range of 5 to 30 degrees.

Referring now to FIG. 7 and 8, the cutting teeth 52 and 62 are seen to be disposed in a sawtooth array and aligned so that the edge of one tooth is offset from the edge of the opposing tooth by the space indicated as dimension C. The dimensions and alignment of the cutting teeth are best seen in FIG. 8 where the illustrated dimensions are as follows:

$\alpha = 30°$
$B = 0.036$ inches
$C = 0.002$ inches
$D = -0.006$ inches
$E = 0.080$ inches The above dimensions and alignment values were determined to be effective for partially shearing a peat moss board having a thickness of about 0.02–0.05 inches and as a basis weight of about 300 g/m$^2$. Other materials may require some adjustment in these values, particularly in regard to roll alignment indicated by dimension C and penetration indicated by dimension D. These and other operating parameters are most readily determined experimentally for any given absorbent board material.

The partial shearing device and its method of operation are more fully described in co-pending and commonly assigned application U.S. Ser. No. (242,274) filed Sept. 12, 1988, which application is incorporated herein by reference for its teaching in this regard.

While the present invention concerning flexible, structurally coherent absorbent materials has been described with particular reference to calendared peat moss boards, it will be appreciated that other friable absorbent materials may also be used. The absorbent material must be susceptible to processing into a relatively thin dense board which is sufficiently friable so that it may be partially severed into strips without cutting or breaking the fibrous reinforcing component. Peat moss boards which are mealy and readily crumbled when not reinforced with a fibrous component are particularly well suited for preparing the absorbent elements of the present invention, but other natural and synthetic absorbent compositions having similar properties can also be used with good results. Accordingly, the present invention is specifically directed to partially severing friable absorbent materials having an integral fibrous reinforcing component into a plurality of strips which are interconnected by said reinforcing component in order to impart flexibility to the absorbent material in a direction transverse to the longitudinal direction of the strips while maintaining sufficient structural integrity in the transverse direction to permit processing and handling of the severed material.

I claim:

1. A flexible absorbent element useful in products for absorbing body fluids comprising a plurality of strips of an absorbent material disposed adjacent to each other and interconnected to one another by a fibrous reinforcing component integral with said absorbent material and extending between said strips to maintain the structural integrity of said absorbent element.

2. The absorbent element of claim 1, wherein said absorbent material comprises peat moss, wood pulp, or a mixture thereof.

3. The absorbent element of claim 1, wherein said reinforcing component comprises natural or synthetic fibers having a length of from about 0.25 to 1.5 inches.

4. The absorbent element of claim 3, wherein said reinforcing component comprises polyester fibers having a denier of from about 1.0 to 5.

5. The absorbent element of claim 4, wherein said polyester fibers have a staple length of from 0.5 to 1.0 inches.

6. The absorbent element of claim 1, wherein said reinforcing component comprises from about 2 to 20% by weight of said absorbent element.

7. The absorbent element of claim 1, wherein said reinforcing component comprises from about 4 to 8% by weight of said absorbent element.

8. The absorbent element of claim 1, wherein said absorbent material comprises calendered peat moss board having a density of from about 0.2 to 1.0 g/cm$^3$.

9. The absorbent element of claim 1, wherein said absorbent material is mechanically deformed in a direction transverse to the longitudinal direction of said strips to impart longitudinal flexibility to said element.

10. The absorbent element of claim 1, wherein said strips have a width of from about 2.0 to 10 mm.

11. The absorbent element of claim 1, wherein said absorbent material has been treated with a wetting agent.

12. The absorbent element of claim 1, wherein said absorbent material includes a layer of Kraft tissue disposed on at least one surface of said absorbent material.

13. The absorbent element of claim 1, wherein said absorbent material includes a layer of Kraft tissue disposed on both surfaces of said material.

14. The absorbent element of claim 1 wherein said absorbent material comprises a mixture of a hydrophilic fibrous component and a superabsorbent polymeric component.

15. The absorbent element of claim 14 wherein said hydrophilic component comprises wood pulp, peat moss or mixtures thereof.

16. The absorbent element of claim 14 wherein said absorbent material comprises wood pulp and hydrogel polymers.

17. The absorbent element of claim 14 wherein said reinforcing component comprises natural or synthetic fiber having a length of from about 0.25 to 1.5 inches.

18. The absorbent element of claim 17 wherein said reinforcing component comprises rayon fibers.

19. The absorbent element of claim 14 wherein said absorbent material has a density of from about 0.2 to 1.0 g/cm$^3$.

* * * * *